(12) United States Patent
Stenton

(10) Patent No.: US 8,518,076 B2
(45) Date of Patent: Aug. 27, 2013

(54) SURGICAL ADHESIVE APPLICATOR

(75) Inventor: Richard J. Stenton, Horrabridge (GB)

(73) Assignee: Advanced Medical Solutions (Plymouth) Limited, Plymouth, Devon (GB)

( * ) Notice: Subject to any disclaimer, the term of this patent is extended or adjusted under 35 U.S.C. 154(b) by 1168 days.

(21) Appl. No.: 11/959,112

(22) Filed: Dec. 18, 2007

(65) Prior Publication Data

US 2008/0167681 A1 Jul. 10, 2008

Related U.S. Application Data

(60) Provisional application No. 60/883,886, filed on Jan. 8, 2007.

(51) Int. Cl.
*A61B 17/08* (2006.01)

(52) U.S. Cl.
USPC .......................................................... 606/214

(58) Field of Classification Search
USPC ................. 606/214; 401/133–134; 222/212, 222/420
See application file for complete search history.

(56) References Cited

U.S. PATENT DOCUMENTS

| | | | | |
|---|---|---|---|---|
| 1,313,566 A | * | 8/1919 | Trobridge | 604/2 |
| 2,737,677 A | * | 3/1956 | Pasulka | 401/205 |
| 2,761,591 A | * | 9/1956 | Du Bois | 222/335 |
| 2,784,127 A | | 3/1957 | Joyner et al. | |
| 3,527,224 A | | 9/1970 | Rabinowitz | |
| 3,591,676 A | | 7/1971 | Hawkins et al. | |
| 3,667,472 A | | 6/1972 | Halpern | |
| 3,995,641 A | | 12/1976 | Kronenthal et al. | |
| 4,035,334 A | | 7/1977 | Davydov et al. | |
| 4,183,684 A | | 1/1980 | Avery, Jr. | |
| 4,444,933 A | | 4/1984 | Columbus et al. | |
| 4,563,104 A | * | 1/1986 | Saint-Amand | 401/139 |
| 4,572,689 A | * | 2/1986 | Chernack | 401/132 |
| 4,650,826 A | | 3/1987 | Waniczek et al. | |
| 4,784,506 A | | 11/1988 | Koreska et al. | |
| 4,785,978 A | * | 11/1988 | Kano et al. | 222/482 |
| 4,925,327 A | * | 5/1990 | Wirt | 401/205 |
| 4,957,385 A | * | 9/1990 | Weinstein | 401/132 |
| 5,480,935 A | | 1/1996 | Greff et al. | |
| 5,538,353 A | | 7/1996 | DeHavilland | |
| 5,582,596 A | | 12/1996 | Fukunaga et al. | |

(Continued)

FOREIGN PATENT DOCUMENTS

| | | |
|---|---|---|
| DE | 4040620 A1 | 7/1991 |
| EP | 0858775 | 8/1998 |

(Continued)

OTHER PUBLICATIONS

Second Collegiate Edition, American Heritage Dictionary, 1976, p. 121.

(Continued)

*Primary Examiner* — Melanie Tyson
*Assistant Examiner* — Son Dang
(74) *Attorney, Agent, or Firm* — Foley & Lardner LLP; Antoinette F. Konski

(57) ABSTRACT

An adhesive applicator for applying medical adhesives, particularly cyanoacrylates, to incisions such as those made during minimally invasive surgery. The applicator employs a pipette tip or similar narrow flow restrictor tip to close the incision and a body of foam to seal the incision. Methods of using the applicator are also disclosed.

15 Claims, 3 Drawing Sheets

(56) References Cited

U.S. PATENT DOCUMENTS

| | | | |
|---|---|---|---|
| 5,658,084 A * | 8/1997 | Wirt | 401/132 |
| D386,849 S * | 11/1997 | Dehavilland | D32/40 |
| 5,752,363 A * | 5/1998 | Edwards et al. | 53/410 |
| 5,762,919 A | 6/1998 | Greff et al. | |
| 5,772,346 A | 6/1998 | Edwards | |
| D396,911 S * | 8/1998 | DeHavilland | D32/52 |
| 5,791,801 A * | 8/1998 | Miller | 401/132 |
| 5,962,010 A | 10/1999 | Greff et al. | |
| 5,975,367 A | 11/1999 | Coelho et al. | |
| 5,976,102 A | 11/1999 | Epstein | |
| 5,998,472 A | 12/1999 | Berger et al. | |
| 6,066,124 A | 5/2000 | Caillouette | |
| 6,283,933 B1 | 9/2001 | D'Alessio et al. | |
| 6,364,163 B1 * | 4/2002 | Mueller | 222/83 |
| 6,475,502 B1 | 11/2002 | Lee et al. | |
| 6,477,743 B1 * | 11/2002 | Gross et al. | 222/525 |
| 6,536,975 B1 | 3/2003 | Tufts | |
| 6,547,467 B2 | 4/2003 | Quintero | |
| 6,592,281 B2 | 7/2003 | Clark et al. | |
| 6,595,940 B1 | 7/2003 | D'Alessio et al. | |
| 6,673,031 B2 | 1/2004 | Mark | |
| 6,705,790 B2 | 3/2004 | Quintero et al. | |
| 6,729,786 B1 | 5/2004 | Tufts et al. | |
| 6,766,817 B2 | 7/2004 | Dias da Silva | |
| 6,918,404 B2 | 7/2005 | Dias da Silva | |
| 6,991,393 B2 | 1/2006 | Tufts et al. | |
| 6,991,394 B2 | 1/2006 | Tufts et al. | |
| 7,044,937 B1 | 5/2006 | Kirwan et al. | |
| 7,066,586 B2 | 6/2006 | Dias da Silva | |
| 7,094,250 B2 | 8/2006 | Stenton | |
| 7,182,536 B2 | 2/2007 | Tufts et al. | |
| 7,306,390 B2 * | 12/2007 | Quintero et al. | 401/133 |
| 7,516,872 B2 * | 4/2009 | Boone et al. | 222/212 |
| 2003/0015557 A1 | 1/2003 | D'Alessio et al. | |
| 2003/0032980 A1 * | 2/2003 | Stenton | 606/213 |
| 2003/0080151 A1 | 5/2003 | D'Alessio et al. | |
| 2003/0236573 A1 | 12/2003 | Evans et al. | |
| 2004/0074925 A1 * | 4/2004 | Faurie | 222/212 |
| 2004/0079766 A1 * | 4/2004 | Kokubo | 222/212 |
| 2004/0254561 A1 | 12/2004 | Stenton | |
| 2005/0025559 A1 * | 2/2005 | Stenton | 401/186 |
| 2005/0047845 A1 | 3/2005 | White et al. | |
| 2006/0049203 A1 | 3/2006 | Boone et al. | |
| 2006/0072959 A1 * | 4/2006 | Tufts et al. | 401/133 |
| 2006/0180613 A1 * | 8/2006 | Manesis | 222/189.09 |
| 2008/0046004 A1 | 2/2008 | Stenton | |

FOREIGN PATENT DOCUMENTS

| | | |
|---|---|---|
| EP | 1445032 A2 | 8/2004 |
| EP | 1 337 455 | 1/2007 |
| JP | 01025843 | 1/1989 |
| WO | WO 95/31138 | 11/1995 |
| WO | WO 96/40797 | 12/1996 |
| WO | WO 02/47602 A2 | 6/2002 |
| WO | WO 2004/110282 | 12/2004 |
| WO | WO/2008/001067 A2 | 1/2008 |

OTHER PUBLICATIONS

Burns et al., "Using Tissue Adhesive for Wound Repair: A Practical Guide to Dermabond," *American Family Physician*, vol. 61, No. 5, Mar. 1, 2000, hand numbered 1-7.

Final Office Action mailed Apr. 18, 2011 in U.S. Appl. No. 11/767,229, filed Jun. 22, 2007.

* cited by examiner

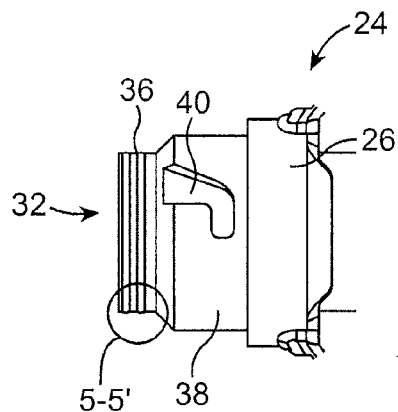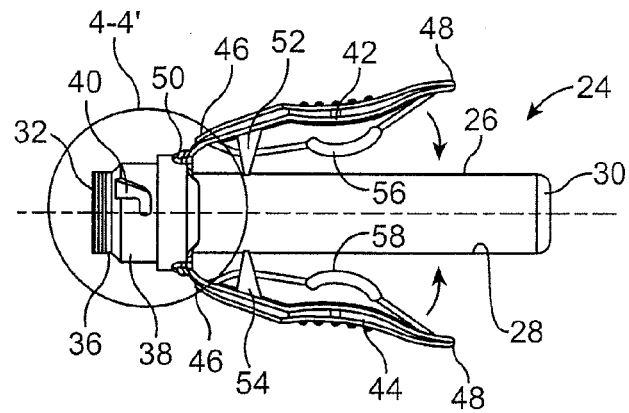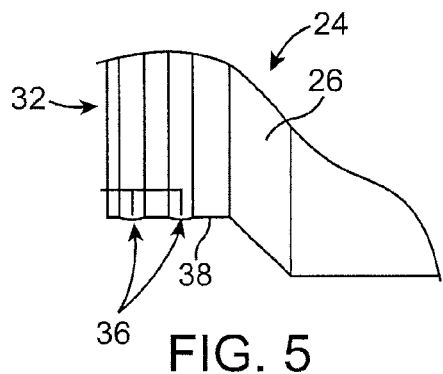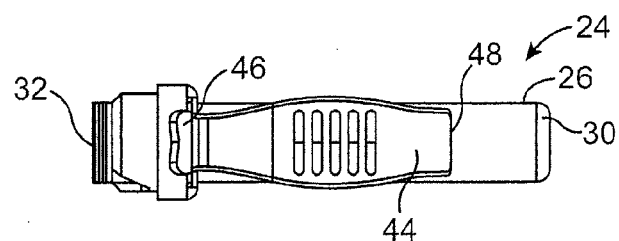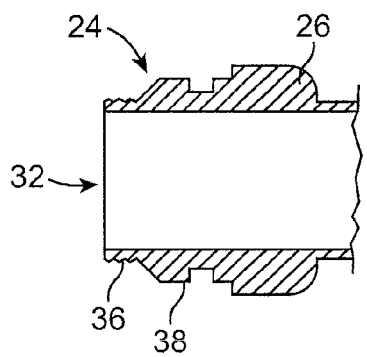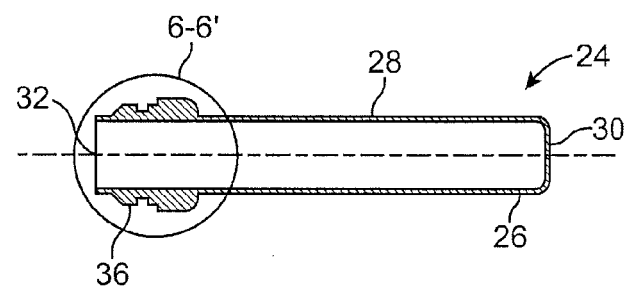
FIG. 4
FIG. 1
FIG. 5
FIG. 2
FIG. 6
FIG. 3

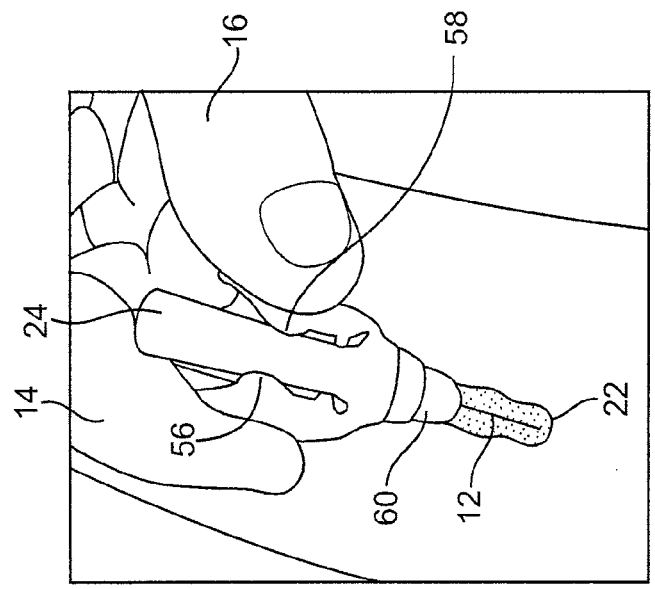
FIG. 8C
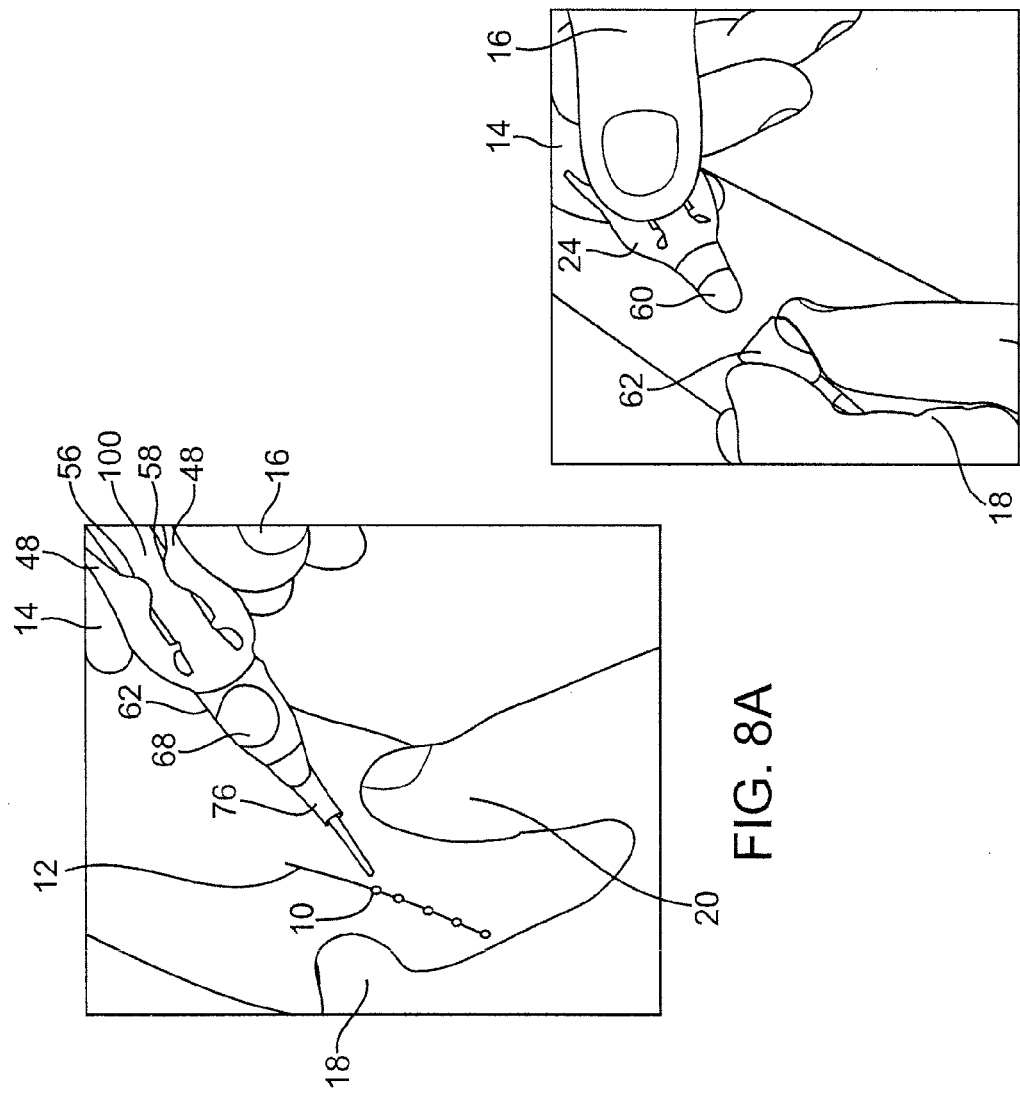
FIG. 8B
FIG. 8A

SURGICAL ADHESIVE APPLICATOR

CROSS-REFERENCE TO RELATED APPLICATION

This application claims benefit under 35 U.S.C. §119(e) of U.S. Provisional Application Ser. No. 60/883,886, filed 8 Jan. 2007, which is hereby incorporated by reference in its entirety.

TECHNICAL FIELD

The present invention relates to applicators for surgical adhesives.

BACKGROUND OF THE INVENTION

Minimally invasive surgery, such as laparoscopic surgery, has become the surgical technique of choice in many situations. In general, minimally invasive surgery is accomplished using small incisions. Minimally invasive surgery often involves the use of specialized equipment and techniques, such as miniature cameras with microscopes, tiny fiber-optic flashlights and high definition monitors. Benefits observed from the use of minimally invasive surgery include minimized pain, faster recovery, and elimination of potential complications associated with traditional surgical techniques.

Minimally invasive surgical procedures can be used in a number of situations including cardiovascular surgery, colon and rectal surgery, gastroenterologic, gynecological surgery, neurosurgery, orthopedic surgery, otorhinolaryngology (ear, nose and throat) surgery, thoracic surgery, urological surgery, and vascular surgery.

A particular type of minimally invasive surgery is laparoscopic surgery. Laparoscopic surgery involves the performance of surgical procedures with the assistance of a video camera and several thin instruments. The use of the camera allows the surgeon to sees images of the patient's body during surgery. During the surgical procedure, small incisions of up to half an inch are made and plastic tubes called ports are placed through these incisions. The camera and the instruments are then introduced through the ports which allow access to the inside of the patient. Laparoscopic surgery is used to perform numerous surgeries such as adrenalectomies, appendectomies, treatment for bowel tumors, lymph node biopsys, gallbladder surgery, hernia repair, treatment for stomach tumors, splenectomies, bariatric surgery, removal of fibroids, removal of benign ovarian cysts, treatment of pelvic endometriosis, fundoplication for gastroesophageal reflux disease (GERD), myotomy for achalasia, nephrectomies, partial nephrectomies, donor nephrectomies, pyeloplasties, and opening of cysts.

The small incisions made during the minimally invasive surgeries can be closed by traditional techniques, such as the introduction of sutures or staples to close the incision wounds. More recently, the use of surgical adhesives has gained favor in closing the incisions. These adhesives are liquid in nature and, upon contact with surface skin proteins and moisture, will polymerize and the resulting polymer bonds strongly to the skin. When applied over apposed skin sections of a wound, the adhesives polymerize and join these apposed skin sections to result in closure of the wound. The adhesives can be formulated to include antimicrobial agents to aid in healing of the wound. The adhesive need not be removed from the wound because it will naturally fall away from the wound as the skin renews itself.

Many different applicators for adhesives have been developed. However, the majority of these applicators do not address the need for a versatile applicator capable of effectively closing and sealing a wound. U.S. Pat. No. 7,094,250, commonly assigned to the assignee of the instant application and incorporated herein by reference, describes an applicator capable of effectively closing, sealing, and dressing a wound using medical adhesive. The present application describes an improvement to the applicator described in the U.S. Pat. No. 7,094,250.

SUMMARY OF THE INVENTION

This invention provides for applicators suitable for use in application of medical adhesive to incisions and methods of using the applicators.

One aspect of the invention provides for an applicator for controllably releasing and applying a surgical adhesive to an incision. In a preferred embodiment, the applicator comprises a receiver having a deformable cylindrical body. The body has a deformable cylindrical wall and a cylinder-closing first end and an open second end. The internal dimensions of the receiver are set to removably accommodate and receive a sealed ampoule of surgical adhesive. The ampoule is formed of a frangible material, which when fractured, releases the surgical adhesive. The receiver's second open end is cylindrical with a series of circumferential sealing ribs present on the outer surface of the second open end. The applicator further comprises a blunt cylindrical body of a surgical adhesive-permeable foam inserted into the open second end of the receiver. The body of foam serves to absorb and transmit adhesive released from the ampoule. The applicator further comprises a cylindrical collar having an open first end and an open second end. The first end of the collar has an internal diameter selected to sealably engage the circumferential sealing ribs and the collar encloses the body of foam material. The second end of the collar has an internal diameter selected to provide a narrowed pathway for the released adhesive to pass when the collar is sealed to the second end of the receiver.

In a preferred embodiment, the applicator additionally comprises a latching slot in the outer surface of the second end of the receiver. The latching slot is located adjacent to the circumferential sealing ribs but is between the circumferential sealing ribs and the first end. The collar has an internally-projecting locking key which fits into the locking slot and locks the collar onto the receiver when the collar is rotated on a common axis between the collar and the receiver. In other preferred embodiments, the applicator additionally comprises a flow restrictor, such as a pipette tip, frictionally attached to the second end of the collar through which surgical adhesive can pass.

In some embodiments, the applicator additionally comprises at least one pressure barb positioned to apply an ampoule-fracturing force to the sealed ampoule. In some embodiments, the applicator comprises at least one pressure pad positioned to apply an adhesive-expressing pressure to the fractured ampoule.

In further preferred embodiments, the applicator additionally comprises a pair of wings, each having an inside and an outside end with the inside end affixed to the receiver at a position adjacent to the open end with the two wings being positioned diametrically across the cylindrical body, with the outside end of the wings being splayed out away from the cylindrical wall but being movable toward the cylindrical wall when a user applies opposing-finger pressure to the outside ends. Each of the wings has a pressure barb facing toward the cylindrical wall. The pressure barb bears upon the cylindrical wall and is capable of applying a compressing force to the cylindrical wall which distorts the cylindrical wall of the cylindrical body. When so distorted, the cylindrical wall applies a fracturing force to an ampoule accommodated and received within the receiver. Preferably, the compressing force to the cylindrical wall applies the fracturing force to the ampoule at a point that is between approximately 4 mm and 8 mm from the end of the ampoule that is closest to the cylinder-closing first end of the body as measured from longest axis of the ampoule. The fracturing force releases surgical adhesive contained within the ampoule. Preferably, each of the wings additionally comprises a pressure pad facing toward the cylindrical wall. The pressure pad bears upon the cylindrical wall and is capable of applying an adhesive-expressing compressing force to the cylindrical wall. This compressing force distorts the cylindrical wall of the cylindrical body and thus applies an adhesive expressing force to the ampoule. The adhesive-expressing force expresses the surgical adhesive contained within the ampoule out of the applicator.

In yet another preferred embodiment, the applicator comprises a receiver having a deformable cylindrical body. The body has a deformable cylindrical wall and a cylinder-closing first end and an open second end. The internal dimensions of the receiver are set to removably accommodate and receive a sealed ampoule of surgical adhesive. The ampoule is formed of a frangible material. The second open end is cylindrical with a series of circumferential sealing ribs present on the outer surface of the second open end and a latching slot in the outer surface of the second end. The latching slot is located adjacent to the circumferential sealing ribs but is between the circumferential sealing ribs and the first end.

The applicator further comprises a pair of wings, each having an inside and an outside end with the inside end affixed to the receiver at a position adjacent to the open end with the two wings being positioned diametrically across the cylindrical body. The outside end of the wings are splayed out away from the cylindrical wall but are movable toward the cylindrical wall when a user applies opposing finger pressure to the outside ends. Each of the wings has a pressure barb facing toward the cylindrical wall. The pressure barb bears upon the cylindrical wall and is capable of applying a compressing force to the cylindrical wall. When thus applied, the compressing force distorts the cylindrical wall of the cylindrical body and applies a fracturing force to an ampoule accommodated and received within the receiver. The fracturing force releases surgical adhesive contained within the ampoule.

The applicator further comprises a blunt cylindrical body of surgical adhesive-permeable foam inserted into the open second end of the receiver. The body of foam serves to absorb and transmit adhesive released from the ampoule. The applicator further comprises a cylindrical collar having an open first end and an open second end. The first end of the cylindrical collar has an internal diameter selected to sealably engage the circumferential sealing ribs and has an internally-projecting locking key which fits into the locking slot and locks the collar onto the receiver when the collar is rotated on a common axis between the collar and the receiver. The collar encloses the body of foam. The second end has an internal diameter selected to provide a narrowed pathway for the adhesive to pass when the collar is sealed to the second end of the receiver. The second end of the collar has a slightly tapered cylindrical shape sized to frictionally and sealably engage a pipette tip or similar flow-focusing nozzle. The pipette tip, when sealed to the collar provides a sealed narrow pathway for surgical adhesive to pass from the receiver through the pipette tip and the collar. When the pipette is removed, there is a broader pathway for the adhesive to pass as a sealing layer from the receiver through the body of foam to the incision.

Another aspect of the invention provides for a method of closing and sealing an incision with an adhesive applicator as described above with a sealed ampoule of surgical adhesive contained in the receiver and the collar and pipette tip in place. A squeezing-together pressure is applied to the wings to produce a compressing force to the cylindrical wall. The compressing force distorts the cylindrical wall of the cylindrical body and applies a fracturing force to the ampoule. The fracturing force releases the surgical adhesive contained within the ampoule. Further pressure can be applied to the wings to cause the pressure pads to supply an adhesive-expressing force to the wall of the fractured ampoule. The expressed adhesive passes through the adhesive-permeable body of foam through the cylindrical collar and through the pipette tip to form the small drops of adhesive. These small drops are applied to the incision to "spot weld" or "suture" it closed. Next, the pipette tip is removed to provide a tip-free applicator. The incision is then sealed by applying a line of adhesive from the tip-free applicator to the incision through the body of adhesive-permeable foam.

In a preferred embodiment, the incision to be closed and sealed is a incision made during laparoscopic surgery. In some embodiments, the surgical adhesive to be applied by the applicator comprises a cyanoacrylate ester, preferably selected from the group consisting of n-butyl cyanoacrylate, 2-octyl, or combinations thereof such as a surgical adhesive comprising 10% 2-octyl cyanoacrylate and 90% n-butyl cyanoacrylate. Preferably, the surgical adhesive to be applied by the applicator comprises a cyanoacrylate ester and an antimicrobial agent.

BRIEF DESCRIPTION OF THE DRAWINGS

This invention will be further described with reference being made to the drawings in which:

FIG. 1 is a top plan view of an ampoule-fracturing receiver employed in the applicator of this invention.

FIG. 2 is a side elevational view of the ampoule-fracturing receiver depicted in FIG. 1.

FIG. 3 is a side cross-sectional view of the ampoule-fracturing receiver depicted in FIGS. 1 and 2.

FIG. 4 is an expanded scale top plan view of the open end portion of the ampoule-fracturing receiver employed in the applicator of this invention taken within the area 4-4' shown in FIG. 1 and showing the circumferential sealing ribs and locking key employed when this receiver is incorporated into the application of this invention.

FIG. 5 is a further expanded scale top plan view of a portion of the ampoule-fracturing receiver employed in the applicator of this invention taken within the area 5-5' shown in FIG. 4 and showing the circumferential sealing ribs employed when this receiver is incorporated into the application of this invention.

FIG. 6 is an expanded scale side cross-sectional view of the open end portion of the ampoule-fracturing receiver employed in the applicator of this invention taken within the area 6-6' shown in FIG. 3 showing the circumferential sealing ribs employed when this receiver is incorporated into the application of this invention.

FIGS. 8A-8C are a series of three perspective views showing A. the applicator of this invention being used to apply small bonding drops of adhesive to a surgical incision, B. the applicator being partially disassembled to reveal a smoothing-strengthening layer applicator and C. the applicator, in its partially disassemble state, being used to apply the strengthening layer to the incision.

DESCRIPTION OF PREFERRED EMBODIMENTS

Figure 7:
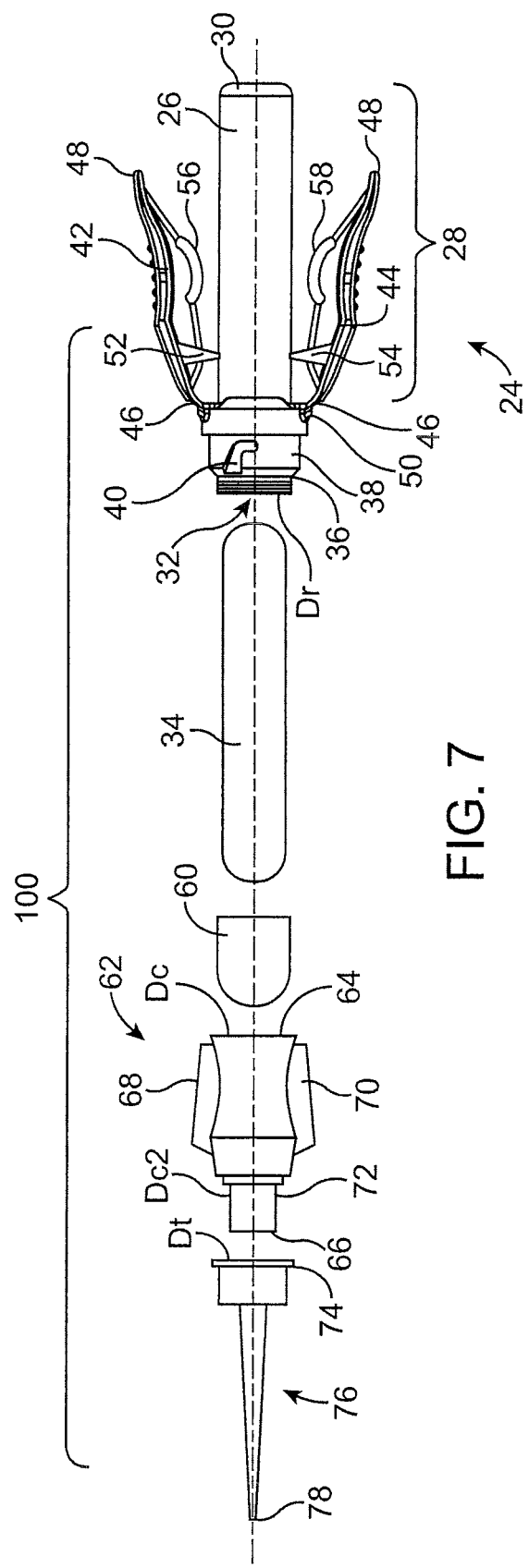
FIG. 7 is an exploded top plan view of the components of the applicator of this invention showing their relationship to the ampoule from which the liquid (adhesive) is released and applied by the applicator.

With reference to the figures, FIG. 7 shows in blown up form an applicator 100 for controllably releasing and applying a surgical adhesive to an incision. The use of such an applicator in this application is illustrated in FIG. 8 where in FIG. 8A the applicator 100 can be seen delivering a series of small drops 10 of adhesive to an incision 12 while being squeezed by fingers 14 and 16. In FIG. 8B, fingers 18 and 20 can be seen partially disassembling the applicator to convert it to a form suitable for delivering a broader strengthening layer 22 of adhesive to the incision 12 as shown in FIG. 8C.

As shown in FIG. 7 and in detailed FIGS. 1 through 6, applicator 100 includes a receiver 24 which a has a deformable cylindrical body 26. Body 26 has a deformable cylindrical wall 28, a cylinder-closing first end 30 and an open second end 32. As shown most clearly in FIG. 7, the internal dimensions of the receiver are selected set to removably accommodate and receive a sealed ampoule 34 of surgical adhesive. Ampoule 34 is formed of a material which can contain the medical adhesive but which is also frangible, that is breakable, in response to pressure applied to it.

The open second end 32 of body 26 is cylindrical. A series of circumferential sealing ribs 36, having a diameter Dr are present on the outer surface 38 of body 26 adjacent to the second open end 32. These ribs provide a sealing surface to which a liquid-tight seal with collar 62 can be formed. These ribs 36 are cast into the body 26 of receiver 24 when it is being formed and thus are made of the same deformable material as body 26. Polypropylene resins, such as Basell Moplen EP548T give good results but, of course, other similar adhesive-compatible resilient plastics may be used. Body 26 carries a latching slot 40 in the outer surface 38. Latching slot 40 is located near the second end 32 of body 26 adjacent to the circumferential sealing ribs 36. This slot is located between the circumferential sealing ribs 36 and the first end 30. It is also to be seen in FIG. 4 that it is located on a portion of the body 26 having a larger diameter than the diameter Dr of the circumferential sealing ribs 36. In this position, the slot can play a part in attaching collar 62 to body 26 without interfering with the sealing action of circumferential sealing ribs 36. This is important because of the nature of surgical adhesives. They are selected because of their ability to adhere to skin. Any inadvertent application of such materials around a surgical site, which could be brought about by interference with the sealing effects of the sealing ribs and subsequent leakage would thus be highly undesirable.

The receiver 26 additionally includes a pair of wings 42 and 44. These wings each have an inside end 46 and an outside end 48. The two inside ends 46 are affixed to the receiver 24 at a position 50 adjacent to the open end 32 with the two wings 42 and 44 being diametrically opposed across the cylindrical body 26 as best illustrated in FIG. 1. The outside ends 48 of the wings 42 and 44 are splayed out away from the cylindrical wall 28 but are movable toward the cylindrical wall 28 when a user applies opposing finger pressure to the outside ends 48 as shown in FIG. 8A.

Each of the wings 42 and 44 has a pressure barb 52 and 54, respectively, projecting "inwards" toward the cylindrical wall 28 of receiver 26. The pressure barbs 52 and 54 bear upon the cylindrical wall 28 in an area close to the second end 32. When the user applies a squeezing-together pressure to the two wings as shown in FIG. 8A these barbs focus this pressure as a compressing force to the cylindrical wall 28, which compressing force distorts the cylindrical wall 28 of the cylindrical body 26 and causes this pressure to be applied as an airpoule-fracturing/fracturing force upon an ampoule 34 accommodated and received within receiver 24. This fracturing force releases surgical adhesive contained within ampoule 34. In a preferred embodiment, the compressing force applied by the barbs when the user applies a squeezing-together pressure to the wings results in a fracturing force applied at a point on the ampoule that is between approximately 4 mm to 8 mm from the end of the ampoule 34 that is closest to the cylinder-closing first end 30 of the body 26 of receiver 24 as measured from longest axis of the ampoule. Application of the fracturing force at this point on the ampoule results in more accurate and reproducible breaking of the ampoule. Application of the fracturing force at positions on the ampoule other than between approximately 4 mm to 8 mm from the end of the ampoule 34 that is closest to the cylinder-closing first end 30 is more likely to result incomplete fracturing of the sealed end of ampoule 34 and less efficient passage of the adhesive through the applicator.

In an alternative embodiment, the applicator comprises multiple barbs for applying the fracturing force to the ampoule. Preferably, the multiple barbs are attached to each other, for example via a ring. In this embodiment, the user applies a squeezing-together pressure to the ring and the multiple barbs focus this pressure as a compressing force to the cylindrical wall 28, which compressing force distorts the cylindrical wall 28 of the cylindrical body 26 and causes this pressure to be applied as an ampoule-fracturing/fracturing force upon an ampoule 34 accommodated and received within receiver 24. Preferably, the compressing force applied by the barbs when the user applies a squeezing-together pressure to the ring results in a fracturing force applied at a point on the ampoule that is between approximately 4 mm to 8 mm from the end of the ampoule 34 that is closest to the cylinder-closing first end 30 of body 26 of receiver 24 as measured from longest axis of the ampoule.

The wings 42 and 44 additionally include pressure pads 56 and 58. These pads also apply a wall-distorting force to wall 28 when the wings 42 and 44 are squeezed together and thus apply pressure on the now-fractured ampoule to express adhesive out of the ampoule through the fracture as shown in FIG. 8.

The released surgical adhesive comes into contact with a blunt cylindrical body 60 of a surgical adhesive-permeable foam inserted into the open second end 32 of receiver 24. The term "foam" is used expansively here and is defined to include any material, such as a sponge or fibrous material, that is permeable to the surgical adhesive and acts as a "wick" absorbing and transmitting the adhesive released from the ampoule. The blunt cylindrical body of foam 60 is held in place in receiver 24 within open end 32 by cylindrical collar 62. This collar has an open first end 64 and an open second end 66. The first end 64 has an internal diameter, Dc, which is selected to sealably engage the circumferential sealing ribs (of diameter Dr) on the receiver 24 in a surgical adhesive-impermeable seal. First end 64 also carries an internally-projecting locking key (not shown) which is sized and positioned to fit into the locking slot 40. This key and locking slot lock the collar 62 onto the receiver 24 when the collar 62 is rotated relative to the receiver 24 on the common axis between the collar 62 and the receiver 24. As shown in FIG. 8B, when the collar and receiver are rotated in the reverse direction relative to one another, the two parts can be separated. Flats or grips 68 and 70 on collar 62 facilitate the user's rotation (and thus locking and unlocking) of the collar 62 relative to receiver 24. The collar 62, when attached to receiver 24, encloses the blunt cylindrical body of foam 60. Second end 66 of collar 62 has a slightly tapered cylindrical outer surface 72 shaped and sized with an average external diameter Dc2 which frictionally and sealably fits into and engages the inside diameter Dt of first end 74 of a flow restrictor such as shown as pipette tip 76. The slightly tapered cylindrical outer surface 72 can be used to apply a line of adhesive that is smaller in width than the line of adhesive that is applied using the blunt cylindrical body of foam 60.

Pipette tip 76, when its first end 74 is sealably-engaged to second end 66 of collar 62, provides a sealed pathway for surgical adhesive to pass from the original ampoule 34 through receiver 24, through the blunt cylindrical body of foam 60 and collar 62 receiver and thence through the flow-restricting pipette tip 76 and outward through end 78 to the surgical incision as a series of fine "spot weld dots" or a fine line of adhesive or the like. When the collar 62 (with pipette tip 76 attached) is removed, as shown in FIG. 8B it exposes the blunt cylindrical body of foam 60. The blunt cylindrical body of foam 60 is saturated with surgical adhesive and when exposed provides a broader pathway for the adhesive to pass from the receiver 24 to the incision 12, now as a sealing-strengthening coating as shown in FIG. 8C.

The blunt cylindrical body of foam 60 can be removed exposing the fractured ampoule 34 which can then be removed from the deformable cylindrical body 26.

Applications and Adhesives

An applicator configured as described herein can be used to close and seal any incision or small wound. The preferred application is the use of the applicator to close and seal incisions made during minimally invasive surgery, such as laparoscopic surgery.

The applicator can be supplied as a preassembled unit comprising the applicator preloaded with a sealed ampoule of surgical adhesive. Alternatively, the applicator can be supplied as an applicator that does not contain a sealed ampoule of surgical adhesive. In this situation, the user, such as a physician, nurse, physician's aid, or clinician, assembles the applicator prior to use so that it contains an ampoule of surgical adhesive.

The applicator is designed to be disassembled after use and the fractured ampoule removed. The fractured ampoule is accessed by rotating the collar and receiver in the reverse direction relative to one another to separate the two parts. As noted above, this step results in the exposure of the blunt cylindrical body of foam which can be used to apply a sealing-strengthening coating of the adhesive. Removal of the foam exposes the fractured ampoule which can then be removed from the deformable cylindrical body, the internal dimensions of which are set to removably accommodate and receive a sealed ampoule of surgical adhesive. Accordingly, one embodiment of the invention provides for disassembling the applicator and removing the fractured ampoule after the applicator has been used to apply the adhesive to the incision.

The applicator is configured for use with liquid surgical adhesive materials. The preferable liquid surgical adhesive materials to be used with the application are liquids containing cyanoacrylate prepolymers.

In situ polymerization of such cyanoacrylate compositions provides for an adherent polymeric film which acts to close and seal the incision. An antimicrobially-effective amount of an antimicrobial iodophore or the like in the cyanoacrylate composition may provide significant enhancements in the effectiveness of the composition as well.

Since the polymeric film is naturally shed from the skin surface two to four days following application, there is no need to effect removal adhesive following surgery, therefore avoiding the skin trauma such as that associated with removal of surgical sutures or staples. Moreover, the addition of antimicrobial agents to the cyanoacrylate composition results in the gradual release of the antimicrobial from the polymerized cyanoacrylate composition, providing antimicrobial at a level that provides protection for post-surgical infection.

Accordingly, the applicator can be used to close and seal an incision in the skin, such as an incision made during laparoscopic surgery, as follows. An applicator, as described herein, with the sealed ampoule of surgical adhesive contained in the receiver of the applicator, is first used to close the incision by applying small drops of adhesive from the applicator to the incision. The small drops of adhesive are produced from the applicator when the user squeezes the wings of the applicator to produce a compressing force to the cylindrical wall. The compressing force distorts the cylindrical wall of the cylindrical body and applies a fracturing force to the ampoule. The fracturing force releases the surgical adhesive contained within the ampoule and the adhesive passes through the adhesive-permeable foam through the cylindrical collar and through the flow restrictor, such as a pipette tip, to form the small drops of adhesive. After the incision is closed using the small drops of adhesive released from the applicator, the user removes the collar from the body of the applicator, thus removing the flow restrictor from the applicator. The removal of the collar and the flow restrictor exposes the surgical adhesive-permeable body of foam. The user then places the body of foam contained at the end of the applicator on the closed incision and applies a line of adhesive to seal and protect the incision.

It may be desirable in some applications to apply an additional layer of adhesive after closing the incision but prior to sealing the incision with adhesive applied through the body of foam. This can be achieved by removing the pipette tip from the applicator and applying the adhesive through the open end of the collar. The resulting band of adhesive is narrower than the band that is applied using the body of foam. After applying this narrower band of adhesive through the open end of the collar, the collar is removed to expose the body of foam and an additional line of adhesive can thus be applied. After completion of the application of the adhesive, the fractured ampoule can be removed by first removing the body of foam to expose the ampoule and subsequently removing the fractured ampoule.

The adhesives which are applied by the applicator of the present invention may preferably comprise a wide variety of cyanoacrylate adhesive formulations. It is to be understood, however, that the present invention is not so limited. Instead, any suitable medical (or non-medical) adhesive can be used.

In accordance with an optional preferred aspect of the present invention, a cyanoacrylate adhesive formulation is used. Preferably, the cyanoacrylate composition used comprises a cyanoacrylate prepolymer composition that can be applied as a liquid to the skin surface Optionally, the cyanoacrylate prepolymer can include therapeutic agents such as analgesics, anti-inflammatory agents, antimicrobial agents, and the like.

Polymerizable cyanoacrylate esters are known in the art and are described in, for example, U.S. Pat. Nos. 3,527,224;

3,591,676; 3,667,472; 3,995,641; 4,035,334; and 4,650,826 the disclosures of each are incorporated herein by reference in their entirety.

The cyanoacrylate composition which finds preferred application using the applicator of this invention comprises a cyanoacrylate ester, which, in monomeric form, is represented by formula I:

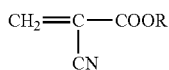

wherein
R is selected from the group consisting of:
 alkyl of 1 to 10 carbon atoms,
 alkenyl of 2 to 10 carbon atoms,
 cycloalkyl groups of from 5 to 8 carbon atoms,
 phenyl,
 2-ethoxyethyl,
 3-methoxybutyl,
and a substituent of the formula:

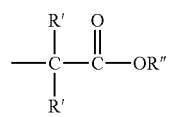

wherein
each R' is independently selected from the group consisting of: hydrogen and methyl, and R" is selected from the group consisting of:
 alkyl of from 1 to 6 carbon atoms,
 alkenyl of from 2 to 6 carbon atoms,
 alkynyl of from 2 to 6 carbon atoms,
 cycloalkyl of from 3 to 8 carbon atoms,
 aralkyl selected from the group consisting of benzyl, methylbenzyl and phenylethyl, phenyl, and
 phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, in the cyanoacrylate esters of formula I, R is alkyl of from 2 to 10 carbon atoms and more preferably alkyl of from 2 to 8 carbon atoms. Even more preferably, R is butyl, pentyl or octyl or a mixture of butyl and octyl (e.g., 2-ethylhexyl) and most preferably R is n-butyl.

It is to be understood that the term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl. Mixtures of such compounds can also be employed as disclosed by Berger, et al., U.S. Pat. No. 5,998,472 which is incorporated herein by reference in its entirety.

A preferred cyanoacrylate ester for use in the invention is n-butyl-2-cyanoacrylate.

In some embodiments, the cyanoacrylate prepolymer composition is a stronger bonding and less flexible cyanoacrylate adhesive composition, such as n-butyl cyanoacrylate. Alternatively, the cyanoacrylate prepolymer is a more flexible cyanoacrylate adhesive, such as an octyl or hexyl cyanoacrylate. In a preferred embodiment, the cyanoacrylate prepolymer composition is a blend of a stronger bonding less flexible cyanoacrylate adhesive composition and a more flexible cyanoacrylate adhesive. Preferably, the cyanoacrylate prepolymer composition is a blend of n-butyl cyanoacrylate and 2-octyl cyanoacrylate, most preferably the cyanoacrylate prepolymer composition is 10% 2-octyl cyanoacrylate and 90% n-butyl cyanoacrylate.

The polymerizable cyanoacrylate esters described herein rapidly polymerize in the presence of water vapor or tissue protein, and the cyanoacrylate bonds to mammalian skin tissue without causing histotoxicity or cytotoxicity. Polymerization occurs at ambient skin temperature while maintaining the skin surface under suitable conditions to allow polymerization to proceed. In general, the length of time required for polymerization will vary depending on factors such as the amount of adhesive composition applied, the temperature of the skin, the moisture content of the skin, the surface area of skin to which the adhesive was applied, and the like. However, polymerization is typically complete within about 10 to about 60 seconds, while the skin is maintained at ambient conditions.

Such polymerizable cyanoacrylate esters are sometimes referred to herein as prepolymers and compositions comprising such esters are sometimes referred to herein as prepolymer compositions.

In preferred embodiments, the sealing-strengthening layer of liquid cyanoacrylate laid down by the applicator has a thickness of no more that about 1 millimeter and yields a polymerized cyanoacrylate composition layer that has a thickness of no more than about 1 millimeter. More preferably, the polymer layer and the liquid layer have a uniform thickness of from about 2 to about 500 µm. Still more preferably, the layers have a thickness of from about 20 to about 100 µm.

Optionally, the cyanoacrylate composition applied by the present applicator can include a "biocompatible plasticizer". As used herein, the term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate, acetyl trihexyl citrate butyl benzyl phthalate, dibutyl phthalate, dioctylphthalate, n-butyryl tri-n-hexyl citrate, diethylene glycol dibenzoate and the like. The particular biocompatible plasticizer employed is not critical and preferred plasticizers include dioctylphthalate and $C_2$-$C_4$-acyl tri-n-hexyl citrates.

Optionally as well, the cyanoacrylate composition applied by the present applicator can include an "antimicrobial agent". As used herein, the term "antimicrobial agent" refers to agents which destroy microbes (i.e., bacteria, fungi, yeasts, prions and viruses) thereby preventing their development and their pathogenic action. In preferred embodiments, the cyanoacrylate composition may contain from about 0.01 to about 5 weight-percent antimicrobial.

Preferred cyanoacrylate compositions useful in the practice of this invention are also disclosed in U.S. Pat. No. 5,480,935, which application is incorporated herein by reference in its entirety. In a particularly preferred embodiment, the cyanoacrylate adhesive composition further comprises an antimicrobially effective amount of a compatible antimicrobial agent. Such compositions preferably comprise from about 0.1 to about 40 and preferably 1 to 30, or more preferably 5 to 20 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. Pat. No. 5,762,919 which is incorporated herein by reference in its entirety.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, it is preferably from about 5 to about 40 weight percent and more preferably from about 10 to about 25 weight percent is added to the cyanoacrylate composition based on the total weight of the composition.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The use of a compatible antimicrobial agent in the composition permits the agent to be released from the polymeric film thereby reducing microbial growth under the film.

Other medicaments suitable for use in conjunction with the cyanoacrylate composition include corticoid steroids such as described by Greff, et al. in U.S. Pat. No. 5,962,010 which is incorporated herein by reference in its entirety and analgesic compounds such as lidocaine. The former reduces inflammation at the site of the application whereas the latter reduces pain. Combinations of a steroid with an analgesic are also covered.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. An applicator for controllably releasing and applying a surgical adhesive to an incision comprising
    a receiver having a deformable cylindrical body, the body having a deformable cylindrical wall and a cylinder-closing first end and an open second end, the internal dimensions of the receiver being set to removably accommodate and receive a sealed ampoule of surgical adhesive, the ampoule being formed of a frangible material which when fractured releases the surgical adhesive,
    the second open end being cylindrical with a series of circumferential sealing ribs present on the outer surface of the second open end,
    a blunt cylindrical body of a surgical adhesive-permeable foam material inserted into the open second end of the receiver to absorb and transmit adhesive released from the ampoule,
    a cylindrical collar having an open first end and an open second end, the first end of the collar having an internal diameter selected to sealably engage the circumferential sealing ribs, the collar enclosing the body of foam material, and the second end of the collar having an internal diameter selected to provide a narrowed pathway for the released adhesive to pass when the collar is sealed to the second end of the receiver,
    a pair of wings, each having an inside and an outside end with the inside end affixed to the receiver at a position adjacent to the open end with the two wings being positioned diametrically across the cylindrical body, with the outside end of the wings being splayed out away from the cylindrical wall but being movable toward the cylindrical wall when a user applies opposing-finger pressure to the outside ends, and
    each of the wings having a pressure barb facing toward the cylindrical wall, the pressure barb bearing upon the cylindrical wall and capable of applying a compressing force to the cylindrical wall, which compressing force distorts the cylindrical wall of the cylindrical body and applies a fracturing force to an ampoule accommodated and received within the receiver, the fracturing force releasing surgical adhesive contained within the ampoule,
    a latching slot in the outer surface of the second end of the receiver, the latching slot located proximal to the collar and distal to the wings and adjacent to the circumferential sealing ribs but being between the circumferential sealing ribs and the first end,
    and the collar having an internally-projecting locking key which fits into the locking slot and locks the collar onto the receiver when the collar is rotated on a common axis between the collar and the receiver,
    wherein the compressing force to the cylindrical wall applies the fracturing force to the ampoule at a point that is between approximately 4 mm and 8 mm from the end of the ampoule that is closest to the cylinder-closing first end of the body as measured from longest axis of the ampoule.

2. The applicator of claim 1, further comprising a flow restrictor frictionally attached to the second end of the collar through which surgical adhesive can pass.

3. The applicator of claim 2, wherein the flow restrictor is a pipette tip.

4. The applicator of any one of claim 1, 2 or 3, further comprising at least one pressure pad positioned to apply an adhesive-expressing pressure to the fractured ampoule.

5. The applicator of claim 1, wherein each of the wings additionally comprises a pressure pad facing toward the cylindrical wall, the pressure pad bearing upon the cylindrical wall and capable of applying an adhesive-expressing compressing force to the cylindrical wall, which adhesive-expressing compressing force distorts the cylindrical wall of the cylindrical body and applies an adhesive expressing force to the ampoule, the adhesive-expressing force expressing surgical adhesive contained within the ampoule out of the applicator.

6. The applicator of claim 1, wherein the surgical adhesive comprises a cyanoacrylate ester, in monomeric form, represented formula I:

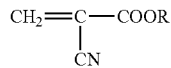

where
R is selected from the group consisting of:
  alkyl of 1 to 10 carbon atoms,
  alkenyl of 2 to 10 carbon atoms,
  cycloalkyl groups of from 5 to 8 carbon atoms,
  phenyl,
  2-ethoxyethyl,
  3-methoxybutyl,
  and a substituent of the formula:

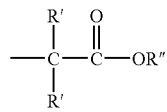

wherein
each R' is independently selected from the group consisting of:
  hydrogen and methyl, and
R" is selected from the group consisting of:
  alkyl of from 1 to 6 carbon atoms,
  alkenyl of from 2 to 6 carbon atoms,
  alkynyl of from 2 to 6 carbon atoms,
  cycloalkyl of from 3 to 8 carbon atoms,
  aralkyl selected from the group consisting of benzyl, methylbenzyl and phenylethyl,
  phenyl, and
  phenyl substituted with 1 to 3 substituents selected from the group consisting of hydroxy, chloro, bromo, nitro, of alkyl 1 to 4 carbon atoms, and alkoxy of from 1 to 4 carbon atoms.

7. The applicator of claim 6, wherein the surgical adhesive comprises a cyanoacrylate adhesive selected from the group consisting of n-butyl cyanoacrylate, 2-octyl cyanoacrylate, and combinations thereof.

8. The applicator of claim 7, wherein the surgical adhesive comprises 10% 2-octyl cyanoacrylate and 90% n-butyl cyanoacrylate.

9. The applicator of claim 6, wherein the surgical adhesive further comprises an antimicrobial agent.

10. A method of closing and sealing an incision with an adhesive applicator comprising
  obtaining the applicator of claim 1 with the sealed ampoule of surgical adhesive contained in the receiver,
  applying a squeezing-together pressure to the wings to produce a compressing force to the cylindrical wall, which compressing force distorts the cylindrical wall of the cylindrical body and applies a fracturing force to the ampoule, the fracturing force releasing the surgical adhesive contained within the ampoule, the adhesive passing through the adhesive-permeable foam through the cylindrical collar and through the pipette tip to form the small drops of adhesive,
  wherein the compressing force applies the fracturing force to the ampoule at a point that is between approximately 4 mm and 8 mm from the end of the ampoule that is closest to the cylinder-closing first end of the body as measured from longest axis of the ampoule,
  closing the incision by applying the small drops of adhesive from the applicator to the incision;
  removing the pipette tip to provide a tip-free applicator, and
  sealing the incision by applying a line of adhesive from the tip-free applicator to the incision through the body of adhesive-permeable foam.

11. The method of claim 10, wherein the incision is an incision made during laparoscopic surgery.

12. The method of claim 10, wherein the surgical adhesive comprises a cyanoacrylate ester, in monomeric form, represented formula I:

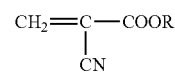

where
R is selected from the group consisting of:
  alkyl of 1 to 10 carbon atoms,
  alkenyl of 2 to 10 carbon atoms,
  cycloalkyl groups of from 5 to 8 carbon atoms,
  phenyl,
  2-ethoxyethyl,
  3-methoxybutyl,
  and a substituent of the formula:

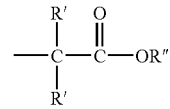

wherein each R' is independently selected from the group consisting of:
  hydrogen and methyl, and
R" is selected from the group consisting of:
  alkyl of from 1 to 6 carbon atoms,
  alkenyl of from 2 to 6 carbon atoms,
  alkynyl of from 2 to 6 carbon atoms,
  cycloalkyl of from 3 to 8 carbon atoms,
  aralkyl selected from the group consisting of benzyl, methylbenzyl and phenylethyl,
  phenyl, and
  phenyl substituted with 1 to 3 substituents selected from the group consisting of hydroxy, chloro, bromo, nitro, of alkyl 1 to 4 carbon atoms, and alkoxy of from 1 to 4 carbon atoms.

13. The method of claim 12, wherein the surgical adhesive comprises a cyanoacrylate adhesive selected from the group consisting of n-butyl cyanoacrylate, 2-octyl cyanoacrylate, and combinations thereof.

14. The method of claim 13, wherein the surgical adhesive comprises 10% 2-octyl cyanoacrylate and 90% n-butyl cyanoacrylate.

15. The method of any of claims 12-14, wherein the surgical adhesive further comprises an antimicrobial agent.

* * * * *